(12) United States Patent
Kishi et al.

(10) Patent No.: US 7,955,321 B2
(45) Date of Patent: Jun. 7, 2011

(54) SURGICAL OPERATION APPARATUS AND MANIPULATOR FOR USE THEREIN

(75) Inventors: Kosuke Kishi, Hitachinaka (JP); Kazuhiro Umekita, Tsuchiura (JP); Kazutoshi Kan, Kawagoe (JP)

(73) Assignee: Hitachi, Ltd., Tokyo (JP)

( * ) Notice: Subject to any disclaimer, the term of this patent is extended or adjusted under 35 U.S.C. 154(b) by 1587 days.

(21) Appl. No.: 11/214,877

(22) Filed: Aug. 31, 2005

(65) Prior Publication Data

US 2006/0155262 A1    Jul. 13, 2006

(30) Foreign Application Priority Data

Jan. 11, 2005 (JP) .................... 2005-003296

(51) Int. Cl.
*A61B 17/00* (2006.01)

(52) U.S. Cl. ............. 606/1; 700/245; 600/410; 600/411

(58) Field of Classification Search .................. 606/427, 606/130, 1; 901/1–18, 30, 41; 414/1; 318/560; 173/2; 81/300; 600/411, 414, 101, 104, 600/109, 410; 700/245–249
See application file for complete search history.

(56) References Cited

U.S. PATENT DOCUMENTS

| | | | | |
|---|---|---|---|---|
| 3,610,058 A * | 10/1971 | Mueller et al. ............... | 74/89.17 |
| 5,339,799 A | 8/1994 | Kami et al. | |
| 5,345,512 A * | 9/1994 | Lee ............................... | 381/377 |
| 5,379,664 A * | 1/1995 | Kershaw et al. ............ | 74/490.05 |
| 5,828,813 A | 10/1998 | Ohm | |
| 6,223,100 B1 * | 4/2001 | Green ............................. | 700/264 |
| 6,394,998 B1 | 5/2002 | Wallace et al. | |
| 6,746,443 B1 | 6/2004 | Morley et al. | |
| 6,913,613 B2 * | 7/2005 | Schwarz et al. ............... | 606/206 |
| 6,994,703 B2 * | 2/2006 | Wang et al. ..................... | 606/10 |
| 2002/0040217 A1 | 4/2002 | Jinno | |
| 2002/0111621 A1 | 8/2002 | Wallace et al. | |
| 2002/0161481 A1 * | 10/2002 | Uratani ......................... | 700/245 |
| 2004/0199147 A1 | 10/2004 | Nishizawa et al. | |
| 2006/0241368 A1 * | 10/2006 | Fichtinger et al. ............ | 600/407 |
| 2007/0156019 A1 * | 7/2007 | Larkin et al. ................... | 600/104 |
| 2007/0293734 A1 * | 12/2007 | Coste-Maniere et al. ..... | 600/300 |

FOREIGN PATENT DOCUMENTS

| | | |
|---|---|---|
| EP | 1 090 594 | 4/2001 |
| EP | 1 477 115 | 11/2004 |
| JP | 8-173442 | 9/1996 |
| JP | 11-267133 | 10/1999 |
| JP | 2002-263109 | 9/2002 |
| JP | 2003-339664 | 12/2003 |
| JP | 2004-122286 | 4/2004 |

* cited by examiner

*Primary Examiner* — Ahmed M Farah
(74) *Attorney, Agent, or Firm* — Antonelli, Terry, Stout & Kraus, LLP.

(57) ABSTRACT

A top end portion of a medical manipulator has a surgical device accessible to a diseased area of a patient. In the manipulator, a pair of rolling members opposing to each other is provided. One of the pair of the rolling members is rolled by a flexible wire relative to the other rolling members. A plate maintains a distance between rotation centers of the pair of the rolling members constant. A pair of gears are held coaxially with the pair of the rolling members respectively, and engaged with each other. A link rotates the gear on an opposite side to a surgical device.

4 Claims, 11 Drawing Sheets

SURGICAL OPERATION APPARATUS AND MANIPULATOR FOR USE THEREIN

The present application claims priority from Japanese application JP2005-3296 filed on Jan. 11, 2005, the content of which is hereby incorporated by reference into this application.

BACKGROUND OF THE INVENTION

The present invention relates to a surgical operation apparatus and a manipulator used in the surgical operation apparatus. In particular, the present invention relates to a medical manipulator.

Japanese Patent Laid-Open No. H11(1999)-267133 discloses an example of a thermal procedure in which a body of a patient is transfixed with a high frequency treatment tool, and a diseased area of the body cavity is treated while observing the diseased area by use of a diagnosis apparatus such as a MRI apparatus, a supersonic scanner and an endoscope. In this procedure, an abdomen of a patient is inflated by means of a pneumoperitoneum method, and a linear treatment applicator and an endoscope are inserted exogenously. While observing markers attached to the treatment applicator by use of an MRI apparatus, the treatment applicator is introduced to the diseased area, which is then treated.

Japanese Patent Laid-Open No. 2003-339664 discloses another example of the thermal treatment. In this treatment, markers which can be recognized by an infrared camera are attached to a rear end of a puncture needle of a treatment tool. In accordance with position information about a puncture needle imaged by the infrared camera and with images acquired by the MRI apparatus, the treatment tool is introduced to the diseased area.

U.S. Pat. No. 6,394,998 and Japanese Patent Laid-Open No. 2004-122286 disclose an example that a medical manipulator is used for treatments. In this manipulator, joints are driven by wires. In consideration of safety and compactness, a driving actuator is prevented from being directly attached to the joint mechanism. In a manipulator disclosed in a U.S. Pat. No. 6,394,998, a top end joint and a surgical device joint provided distally of the top end joint are pivoted and opened and closed by use of wires. In a manipulator disclosed in a Japanese Patent Laid-Open No. 2004-122286, transmission lengths and phases of driving wires are maintained constant regardless of a change of an angle of the joint by use of two rolling members.

Since the conventional surgical devices for thermal treatments, disclosed in Japanese Patent Laid-Open No. H11 (1999)-267133 and Japanese Patent Laid-Open No. 2003-339664 have a linear shape, it is sometimes difficult that the surgical device approaches a target diseased area while avoiding organs, blood vessels, and so on (hereinafter called obstacles) which are not diseased and thus cannot be injured. Additionally, a puncture attitude of the surgical device is limited. When the surgical device is introduced to a diseased area, a position of a top end of the surgical device is recognized by use of MRI tomographic images. In some cases, it takes long time to find markers placed near the top end of the surgical device from many MRI tomographic images.

A surgical device attached to a top end portion of a medical manipulator is required to be compact and to have a plurality of degrees of freedom. In the manipulator disclosed in U.S. Pat. No. 6,394,998 and Japanese Patent Laid-Open No. 2004-122286, when driving power is transmitted from a bending joint to a top end joint next to the bending joint, the driving power is transmitted from the bending joint to a surgical device by use of wires. When the driving power is transmitted through the bending joint by use of wires, the wires may be fatigued and worn to brake. A joint mechanism such as a surgical device using wires having thin diameters needs to be often maintained.

BRIEF SUMMARY OF THE INVENTION

The present invention is achieved to solve the problems of the related arts. An object of the invention is to make a surgical operation manipulator compact and to increase the maintainability. Another object of the invention is to improve convenience of a surgical operation manipulator.

A characteristic of the invention for achieving the objects is as follows. In a surgical operation apparatus including a surgical operation manipulator, the manipulator has a plurality of joint portions which can bend and translate or oscillate. The joint portions are driven from the outside by means of at least one of a link mechanism and a rack-and-pinion mechanism.

In this characteristic, the joint portion has a pair of gears engaged with each other, a plate member to which the pair of the gears are attached, a small gear integrally formed to one of the pair of the gears, a flexible rack engaged with the small gear, a first link whose one end portion is attached to the other of the pair of the gears, and a second link whose one end portion is attached to the plate member. It is preferable that a bending movement becomes possible by driving the first link, and a translation movement becomes possible by driving the second link. Driven rollers or driven gears are attached to the other end portions of the first and second links. Driving rollers or driving gears are provided in rolling contact with the driven rollers or driven gears. Pulleys for driving the driving rollers or driving gears and flexible wires mounted to the pulleys may be provided.

In the characteristic, the joint portion has two pairs of gears engaged with each other, a plate member to which each pair of the gears is attached separately, a roller and plate member which are placed between the two pairs of the gears and in rolling contact with each other, a small gear which is engaged with one of a pair of gears and integrated with a first bevel gear, and a second bevel gear which is engaged with the first bevel gear integrally formed to the small gear and has a grip portion extending radially outward. A bending movement may be possible by driving the roller. A gripping movement may be possible by driving the pair of the gears.

In the characteristic, a top end portion of the manipulator can hold a surgical device. The joint portion may have a pair of rolling members placed opposite to each other, first driving means for causing one of the rolling members to roll relative to the other rolling member, maintaining means for maintaining a distance between the pair of the rolling members, a pair of gears each of which is coaxially formed to each of the rolling members and engaged with each other, and second driving means for driving the gear on the opposite side to the surgical device. The joint portion may have a pair of gears engaged with each other, a pair of links each of which holds each of the pair of the gears, a member for causing the pair of the links to be in rolling contact, maintaining means for maintaining a distance between the pair of the gears constant, and driving means for driving one of the gears and one of the maintaining means. Further, a small gear is formed to the gear on the side of the surgical device, the gear being one of the pair of the gears. A flexible rack engaged with the small gear, and a guide for movably holding the rack and a pinion may be provided.

Another characteristic of the invention for achieving the objects is as follows. A diagnostic imaging apparatus for detecting a condition of a patient and making the condition visible, a surgical device accessible to a diseased area of a patient, a manipulator whose top end portion has the surgical device, and a control portion for driving and controlling the manipulator are provided. The manipulator enables the surgical device to bend and translate in a body cavity of a patient. The diagnostic imaging apparatus is preferably a MRI apparatus. Markers which can be recognized by the MRI apparatus may be placed to a guide member for guiding an exchangeable linear surgical device near the surgical device.

A further characteristic of the invention for achieving the objects is a manipulator whose top end portion has a surgical device accessible to a diseased area of a patient. In the manipulator, a pair of rolling members placed opposite to each other, first driving means for causing one of the rolling members to roll relative to the other of the rolling members, means for maintaining a distance between rotation centers of the pair of the rolling members constant, a pair of gears each of which is coaxially held with each of the pair of the rolling members and which are engaged with each other, and second means for rotating the gear on the opposite side to the surgical device, are provided.

A further characteristic of the invention for achieving the objects is as follows. A small gear coaxially formed to a gear placed on a side of a surgical device, a rack flexibly formed to be engaged with the small gear, and a rack guide which moves in synchronization with a rolling member on a side of the surgical device are provided. In this characteristic, the surgical device is exchangeably connected to the flexible rack. The rack is driven to make the surgical device translate. The surgical device may be exchangeable.

According to the present invention, a bendable joint apparatus is provided to a manipulator of a surgical operation apparatus. A surgical device positioned on a top end portion of the manipulator is driven by a wire. The joint apparatus is driven without a wire. Accordingly, an attitude range of the surgical device is increased, and convenience of the manipulator is improved. Additionally, the surgical operation apparatus is made compact, and the maintainability of the surgical operation apparatus is improved.

BRIEF DESCRIPTION OF THE SEVERAL VIEWS OF THE INVENTION

DETAILED DESCRIPTION OF THE INVENTION

Figure 1:
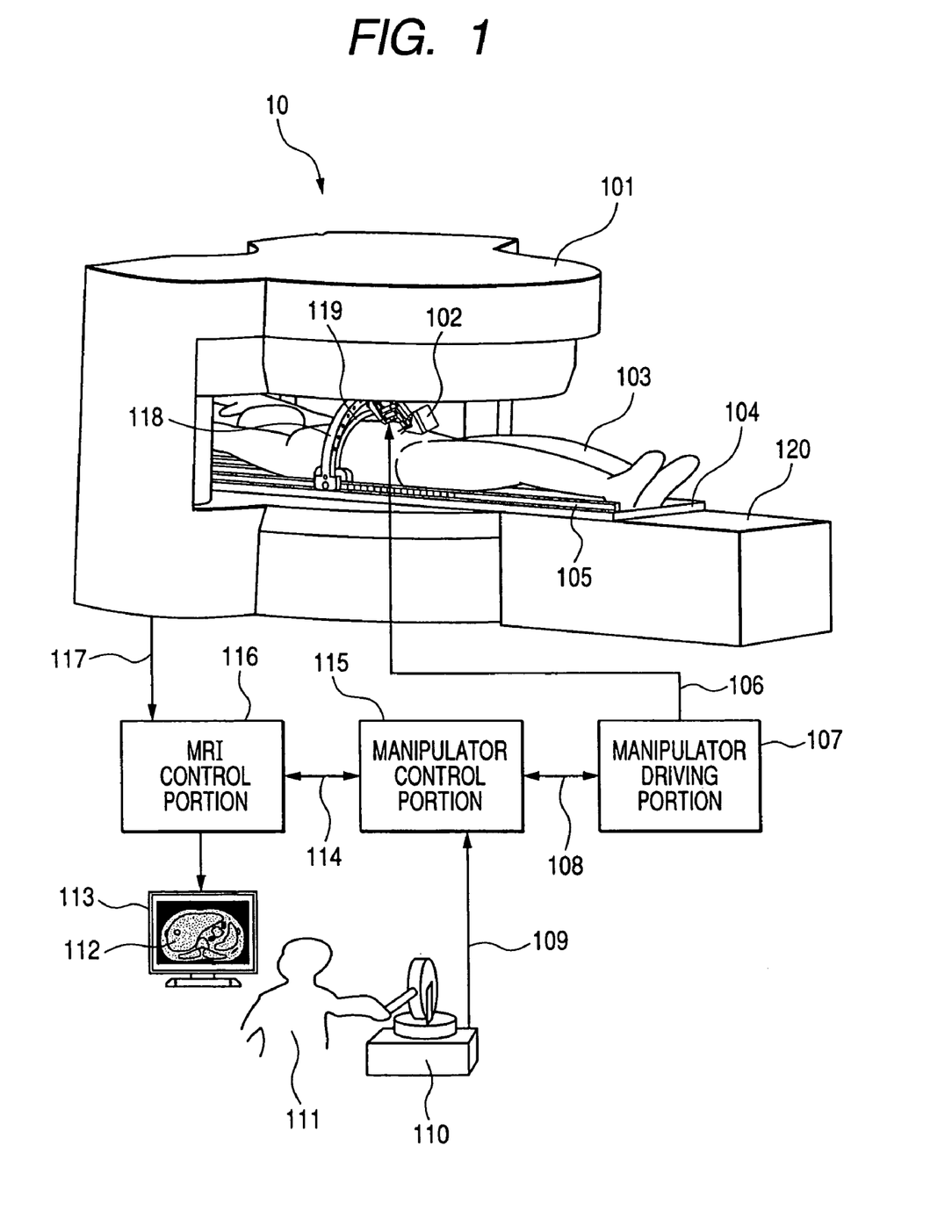
FIG. 1 is a block diagram of one embodiment of a surgical operation system of the present invention.

One embodiment of a surgical operation apparatus 10 of the present invention is explained below in reference to the drawings. FIG. 1 is a block diagram showing a surgical operation system to which the surgical operation apparatus is applied. In an open type MRI apparatus 101 in which magnets are oppositely placed one above another, a bed plate 104 which can move in the horizontal direction and on which a patient 103 is mounted is placed on a surgical operation bed 120. A diseased area of the patient 103 is positioned in a pickup position which is set between the magnets of the MRI apparatus 101. The MRI apparatus 101 picks up an image of the diseased area. The image of the diseased area is detected as a resonance signal. The detected signal is transmitted to an MRI control portion 116 via a transmission line 117. The MRI control portion 116 executes signal processing such as image processing. The processed signal is displayed as an image 112 on an image information display portion 113.

The surgical operation apparatus 10 shown in this embodiment has a surgical operation manipulator 102. One end portion of the surgical operation manipulator 102 is fixed to the bed plate 104. The surgical operation manipulator 102 is connected to a manipulator driving portion 107 via a signal line 106. A manipulator control portion 115 is connected to the manipulator driving portion 107 via a transmission line 108. The manipulator control portion 115 is connected to the MRI control portion 116 via a transmission line 114, and also to an operation input device 110 via a transmission line 109.

In the open type MRI apparatus 101, an RF reception coil 119 for receiving front signals is provided in a form of a ring. A guide frame 118 is installed covering a periphery of the RF reception coil 119. The guide frame 118 can be fixed to any position of a guide rail 105 which is attached to the bed 120 and extends in the longitudinal direction. To acquire attachment position information when the guide rail 105 is attached to the guide frame 118, a position sensor is provided, or a scale is provided to the guide rail 105.

An operator 111 operates the operation input device 110 with seeing the image 112 displayed on the image information display portion 113. When the operator 111 operates the operation input device 110, an operation input signal is generated. The operation input signal is transmitted to the manipulator control portion 115 via the transmission line 109. The manipulator control portion 115 generates an operation command control signal of the manipulator 102 in accordance with the operation input signal and with joint value information about each joint of the manipulator 102. The joint value information is detected by the manipulator driving portion 115. The converted operation command control signal is transmitted to the manipulator driving portion 107 via the transmission line 108.

The manipulator driving portion 107 provides a power for driving each joint of the manipulator 102 by means of a tendon-sheath transmission method. Data of each joint of the manipulator is detected by a sensor (not shown) attached to the manipulator driving portion 107. The detected data is transmitted to the manipulator control portion 115 via the transmission line 108.

Not to prevent the open type MRI apparatus 101 from detecting signals, the manipulator driving portion 107 and the manipulator control portion 115 provide electrical isolation appropriately. The manipulator control portion 115 is placed outside a shield room (not shown) formed covering the open type MRI apparatus 101. Certainly shielded control line and signal line are introduced to the manipulator driving portion 107 through a waveguide (not shown). Alternatively, a conductive panel grounded inside or outside the shield room is provided. A connector is attached to the conductive panel to input and output signals. A material of the conductive panel is non-magnetic so that the surgical operation bed 120 and the manipulator 102 can operate near the MRI apparatus 101. For example, titanium, duralumin, or brass is used in the metal portion requiring a strength. A low-magnetic and insulating material such as engineering plastic is used in the other portion.

Figure 2:
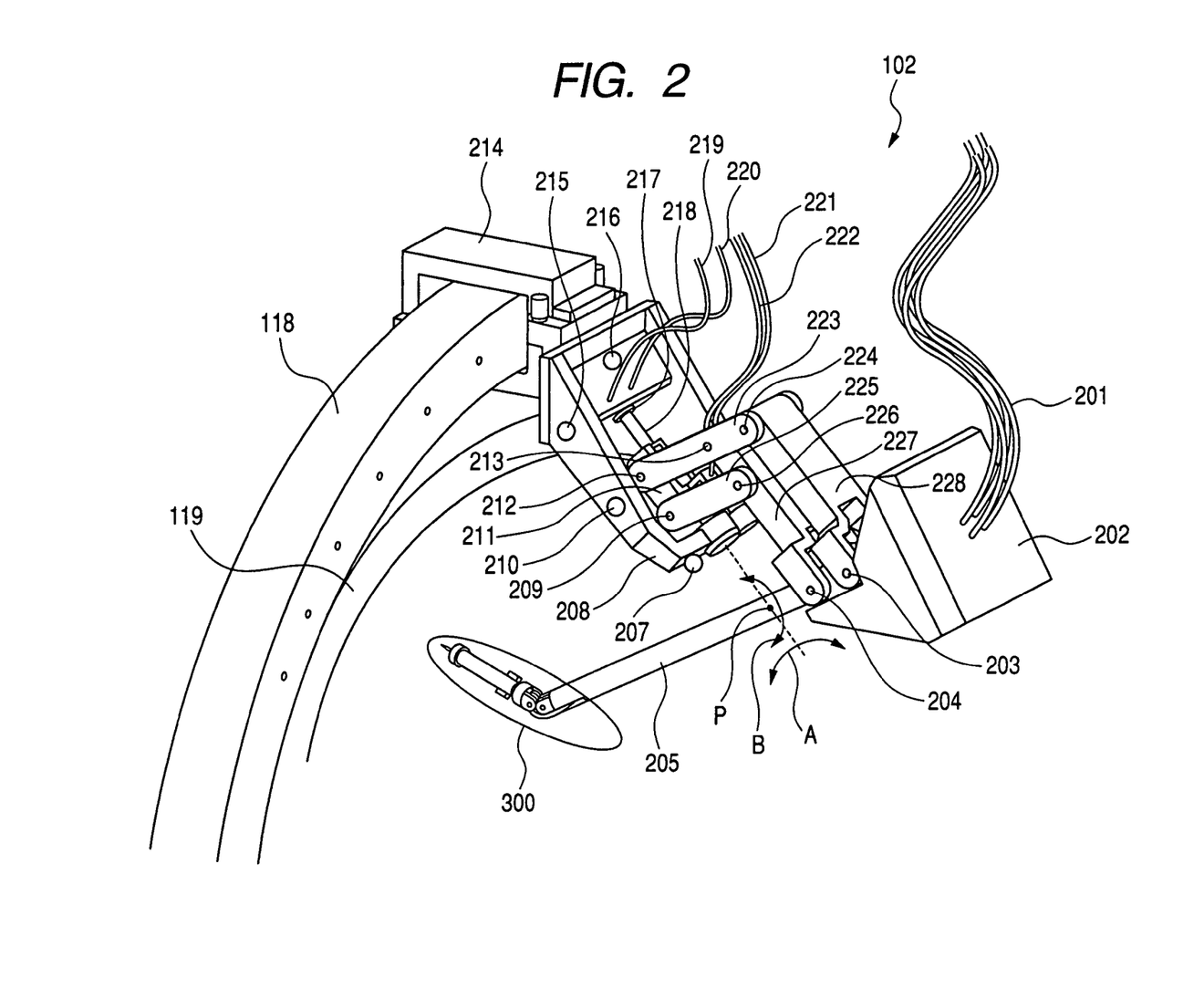
FIG. 2 is a perspective view of a surgical operation supporting manipulator used for the surgical operation system shown in FIG. 1.

FIG. 2 is a perspective view showing in detail the manipulator 102 used for the surgical operation apparatus 10 shown in FIG. 1. The manipulator 102 is made compact so that the manipulator 102 can be placed within a capture area of the open type MRI apparatus 101. A base portion of the manipulator 102 is fixed to the guide frame 118 by use of a fixture 214. To detect the fixing position when the fixture 214 is fixed to the guide frame 118, a scale is provided to the guide frame 118, or a position sensor is provided to at least one of the guide frame 118 and manipulator 102.

A manipulator frame 208 which contains each member used for a joint of the base portion of the manipulator 102 is attached to the fixture 214. Markers 207, 210, 215, and 216 are attached to a side surface portion of the manipulator frame 208 and to an opposite surface to the fixture so that a diagnostic imaging apparatus (not shown) can recognize a position of the manipulator 102. A position of the manipulator 102, the position being detected in accordance with the markers 207, 210, 215, and 216, is displayed by means of a coordinate system which is set in the diagnostic imaging apparatus. The coordinate system which is set in the diagnostic imaging apparatus is converted to a coordinate system which is set in the manipulator 102, or a coordinate system of the manipulator 102 is converted to a coordinate system of the diagnostic imaging apparatus, so that information about the manipulator 102 can be displayed on the diagnostic imaging apparatus by means of computer graphics. Accordingly, the manipulator information can be displayed over an MRI image.

A joint shaft 218 of a first joint is rotatably attached to the manipulator frame 208 via a bearing (not shown). A pulley 217 is fixed to the joint shaft 218. A resin wire (not shown) is mounted to the pulley 217. The resin wire passes in resin flexible tubes 219, 220, and is introduced to a motor 507, which is described later. A base 211 of a second joint is fixed to an end portion of the joint shaft 218. The base 211 of the second joint rotates with the joint shaft 218.

One end portion of a long link 223 is pivotally attached to the base 211 of the second joint by use of a shaft 212. One end portion of a short link 225 is pivotally attached to the base 211 of the second joint by use of a shaft 209. The other end portion of the long link 223 is attached to one end portion of a link 228 by use of a shaft 224. The other end portion of the short link 225 is attached to one end portion of a link 227 by use of a shaft 226. The other end portions of the links 227 and 228 are pivotally attached to the guide 802 (see FIG. 6) attached to the surgical device shaft 205 by use of shafts 204 and 203. The long link 223 is also attached to the link 227 by use of a shaft 213. The short link 225 is attached to a middle portion of the link 227. As a result, the links 227 and 228 can move in parallel with each other.

A top end portion of the surgical device shaft 205 has a bend translation joint 300. The surgical device is attached to a top end portion of the bend translation joint 300. A surgical device drive relaying portion 202 is provided to a side of the surgical device 205, the side being provided with the links 227 and 228. The surgical device drive relaying portion 202 has a plurality of flexible tubes 201 into which wires for driving the surgical device are inserted.

The links 223, 225, 227, and 228, and the surgical device shaft 205 form a parallel link. When the long link 223 and short link 225 rotate about the shafts 209 and 212, the surgical device shaft 205 moves with maintaining, relative to the base 211, the same angle as an angle of the links 223 and 225 relative to the base 211.

A pulley (not shown) is fixed to the shaft 212 for attaching the long link 223 to the base 211. A resin wire is wound about the pulley. The wire wound about the pulley is inserted into tubes 221, 222, and introduced to a driving source. When the shaft 212 is driven to rotate by use of the wire, the long link 223 rotates about the shaft 212. A wire is wound about a pulley (not shown) coaxially attached to the shaft 209, and introduced into the tubes 221 and 222. When the wire is pulled, the shaft 209 rotates to move the link 225. At this time, the link 223 forming the parallel link with the link 225 also moves. accordingly, the surgical device shaft 205 pivots.

When a pivot point of the pivot is P, the surgical device shaft 205 can rotate about the point P in two directions A and B. When the surgical device shaft 205 is inserted into a body cavity of the patient 103, the manipulator 102 is initially set so that a position of the pivot point P coincides with a hole of the body surface. Accordingly, minimally invasive surgery is possible without large wounds. Since the movement in the direction A is generated by the shaft 218, members for generating this movement in the direction A are also called a joint A. Since the movement in the direction B is generated by use of the links 223 and 225 and their attachment shafts 212 and 209, members for generating this movement in the direction B are also called a joint B.

Figure 3:
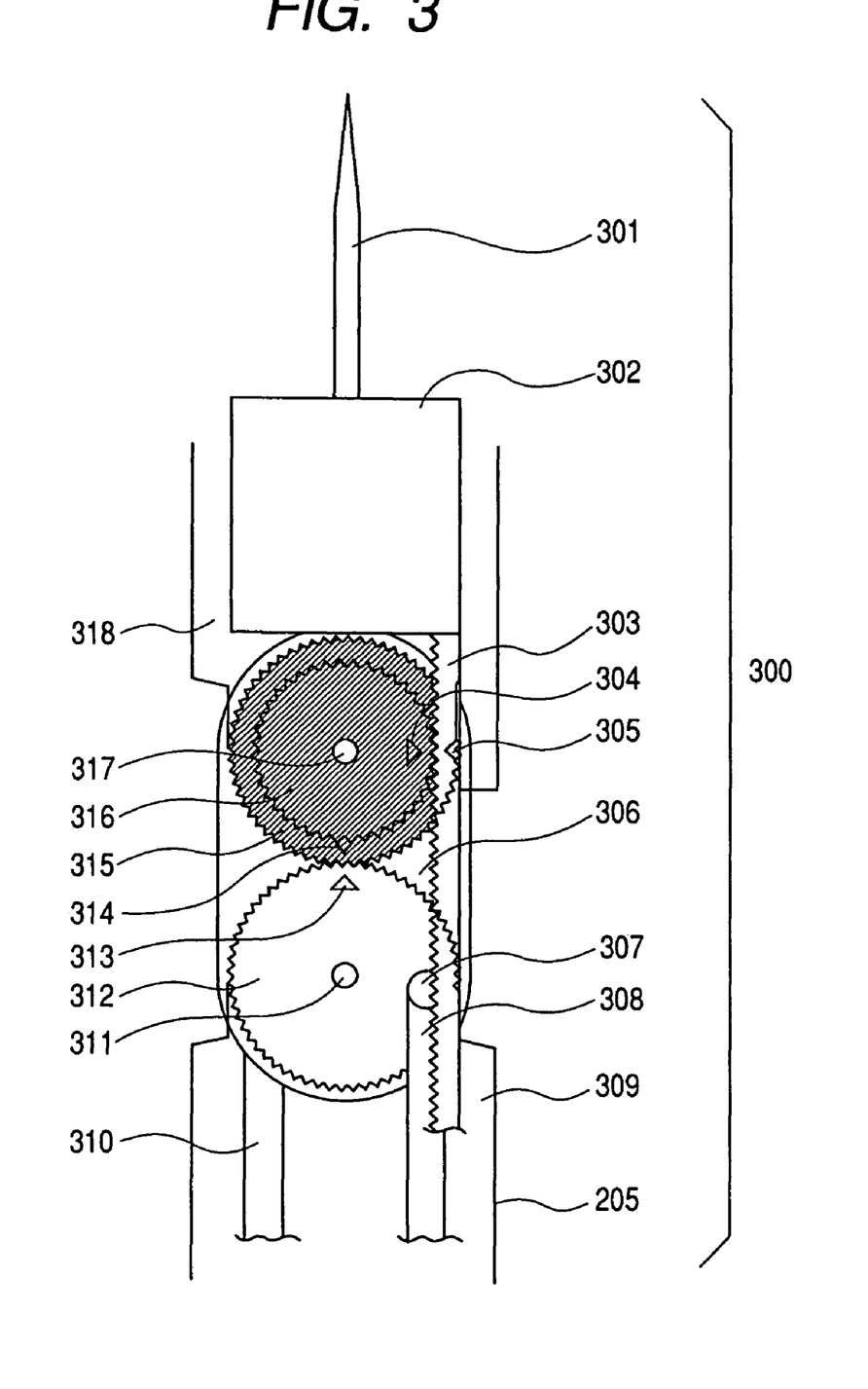
FIG. 3 is a front view for explaining movements of a joint device.
Figure 4:
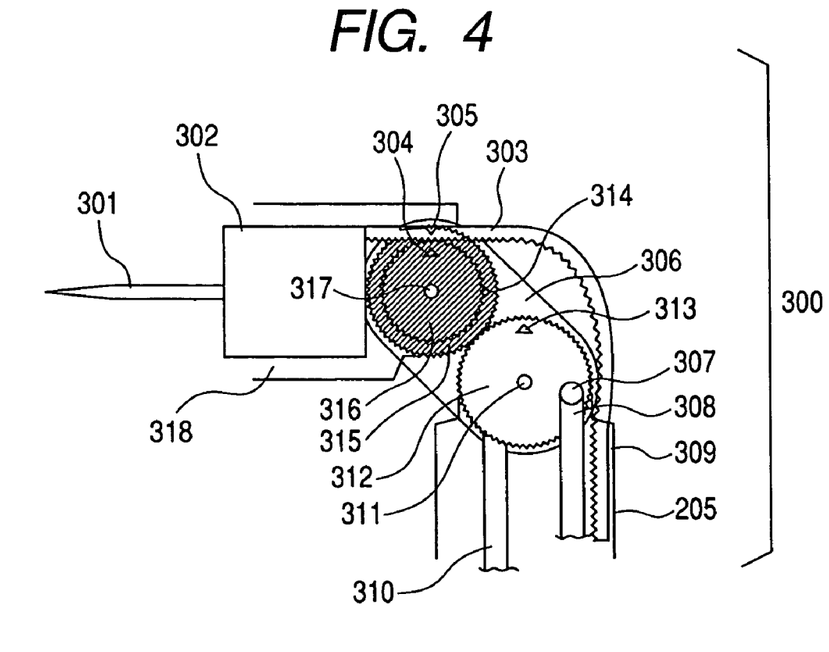
FIG. 4 is a front view for explaining movements of the joint device.
Figure 5:
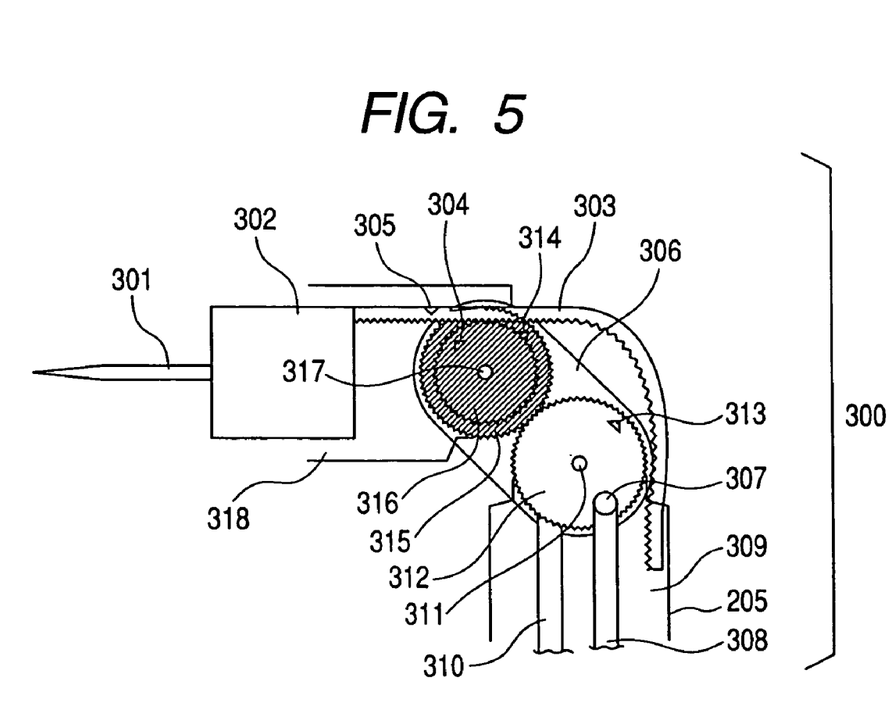
FIG. 5 is a front view for explaining movements of the joint device.

A general structure and operations of the bend translation joint 300 attached to the top end portion of the surgical device shaft 205 are explained below in reference to FIGS. 3 to 5. FIG. 3 is a front view of a base position where the bend translation joint 300 and the surgical device shaft 205 are aligned with each other. FIGS. 4 and 5 are front views where the joint portion is bended. The bend translation joint 300 enables a puncture needle to translate and bend. The puncture needle is attached to the top end portion of the bend translation joint 300.

The bend translation joint 300 has a pair of gears 312, 315 which have the same shape. The pair of the gears 312, 315 are engaged with each other, and attached to pins 311, 317 attached to an elliptic plate 306. A small gear 316 is coaxially attached to the gear 315, and rotates in synchronization with the gear 315.

A flexible resin rack 303 is engaged with the small gear 316. The flexible resin rack 303 is such that a rack is formed on a flexibly bendable resin stick. A shank 302 to which the puncture needle 301 is attached is connected to a top end portion of the rack 303. To contain the flexible rack 303 in the surgical device shaft 205 without fixing the rack 303, slits on which the rack 303 is smoothly passed are formed on the surgical device shaft 205 and the bearing member 309. To cool or heat a top end of the puncture needle 301, an electrical wire and a waterway may be provided to the shank 302. The electrical wire and waterway may be provided to the flexible rack 303.

A translation guide 318 which controls movement of the shank 302 is provided to a periphery of the shank 302. The translation guide 318 is attached to the pin 317 to which the gear 315 on a side of the puncture needle 301 is attached. Bearing members 309, which are a pair of projecting portions opposed to each other, are provided to the top end portion of the surgical device shaft 205. A bearing which rotatably supports both end portions of the pin 311 is held on middle portion of the bearing member 309.

One end of a gear driving link 308 is rotatably fixed to a front surface of the gear 312 on a side of the surgical device shaft 205 by use of a pin 307. One end of a plate driving link 310 is pivotally fixed to a back side of a plate 306 by use of a pin (not shown).

Labels 313 and 314 having an outward triangular shape are affixed near peripheries of the pair of the gears 312 and 315. The labels 313 and 314 are affixed so that they are opposed to each other when the bend translation joint 300 is straight in a base position. Labels 304 and 305, which are the same as the labels 313 and 314, are affixed near an periphery of the small gear 316 and to the rack 303. The labels 304 and 305 is affixed so that they are opposed to each other when the bend translation joint 300 is in a base position. By use of the labels 304, 305, 314, and 315, movement of each portion is visible.

In the bend translation joint 300, when the gear driving link 308 is moved, the gear 312 rotates about the pin 311. FIG. 4 shows this state. When the plate driving link 310 is pulled in the direction of the surgical device shaft 205, the plate 306 rotates about the pin 311 to which the gear 312 on the side of the surgical device shaft 205 is attached. At this time, the other pin 317 attached to the plate 306, the gear 315 attached to the pin 317, the small gear 316, and the translation guide 318 try to move simultaneously.

However, when the gear driving link 308 is not moved, the gear 312 is kept to be fixed, and thus does not rotate. The gear 315 attached to the plate 306 via the pin 317 is engaged with the other gear 312 to rotate, and follows movement of the plate 306. The translation guide 318 rotates about the pin 317 relative to the plate 306 by an angle by which the plate 306 moves relative to the bearing member 309. Therefore, when the gear 315 rotates about the gear 312 by an angle of 45 degrees, the translation guide 318 tilts by 90 degrees relative to the bearing member 309.

Even when the translation guide 318 rotates about the pin 317, an engagement position between the small gear 316 integrated with the gear 315 and the flexible resin rack 303 contained in the translation guide 318 does not change. As a result, a relative position between the puncture needle 301 connected to the flexible resin rack 303 and the translation guide 318 does not change. A top end portion of the flexible resin rack 303 is contained in the bearing member 309 freely. Therefore, the flexible resin rack 303 can move in the axial direction of the surgical device shaft 205. When the translation guide 318 tilts, the flexible resin rack 303 bends to be pulled out of the bearing member 309 in some degree. Accordingly, the rack 303 and small gear 316 do not interfere with a bending drive which tilts an attitude of the puncture needle 301.

A movement for projecting the puncture needle 301 after tilting the puncture needle 301 relative to the surgical device shaft 205 is explained in reference to FIG. 5. A position of the plate driving link 310 is fixed to move the gear driving link 308 in the direction of the surgical device shaft 205. The gear 312 on the side of the surgical device shaft 205 rotates about the pin 311. The gear 315 on the side of the puncture needle 301, the gear 315 being engaged with the gear 312 on the side of the surgical device shaft 205, rotates about the pin 317. The small gear 316 integrated with the gear 315 on the side of the puncture needle 301 also rotates about the pin 317. When the small gear 316 rotates, an engagement position of the resin rack 303 engaged with the small gear 316 changes. Then, the resin rack 303 is pushed to the left of FIG. 5. As a result, the puncture needle 301 projects via the shank 302. When the gear driving link 308 moves in the direction of the puncture needle 301, the puncture needle 301 is drawn in the direction of the translation guide 318.

In the explanation for the bending movement and projecting and drawing movements of the puncture needle 301, components of the bend translation joint 300 are partially abbreviated to make the explanation simple. In the perspective view of the manipulator of FIGS. 6 and 7, the other mechanism components are also shown. For example, since a case in which it is difficult to maintain a position of the bend translation joint 300 by use of only the engagement of the pair of the gears 312 and 315 is assumed, rolling contact members 309a and 318a, in addition to the gears 312 and 315, are attached to the pins 317 and 311. The rolling contact members 309a and 318a are planes having a predetermined thickness and having semicircular portions where the rolling contact members 309a and 318a are in contact with each other. Since the rolling contact members 309a and 318a do not slide, but are rolling contact with each other, an angle between the translation guide 318 and plate 306 is maintained. The puncture needle is about 5 cm long. The shank 302 is a little less than 2 cm long.

The bend translation joint 300 shown in this embodiment can bend and translate while the bend and translation do not interfere with each other. Therefore, each shaft does not need to be cooperatively controlled. The controllability increases. Even a surgical device such as the puncture needle 301 positioned distally of the bending joint having the plate 306 and gears 312 and 315 can be driven without passing a wire through the bending joint. Accordingly, a fatigue breakage, slack, or the like of the wire can be avoided to increase the maintainability. In this embodiment, the link mechanism is used for driving the bending portion and gears. A driving mechanism such as wires and belts can be used.

Figure 6:
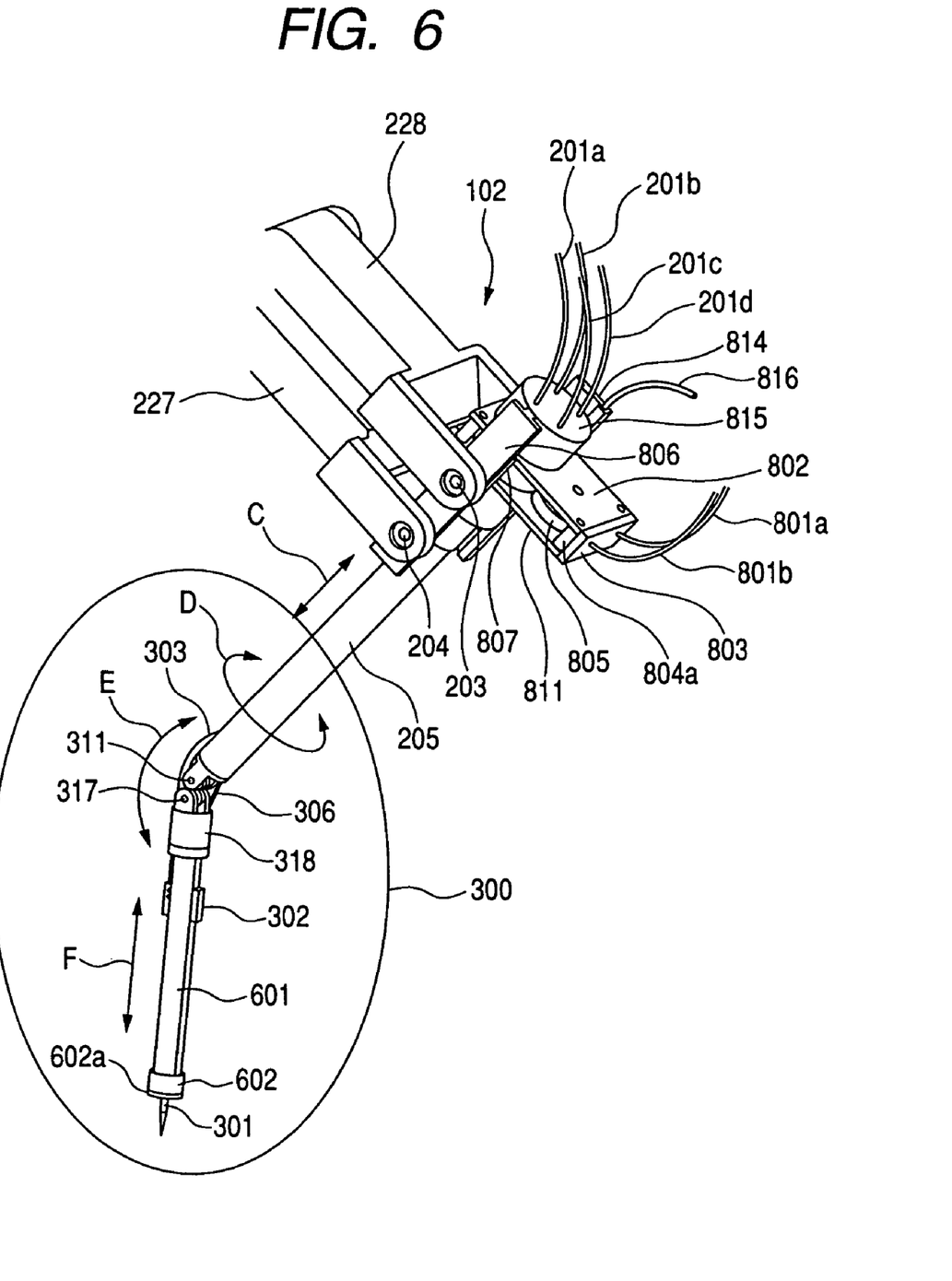
FIG. 6 shows a perspective view of a surgical device manipulator used for the surgical operation system shown in FIG. 1.

FIG. 6 is a perspective view showing the manipulator 102 in detail. The surgical device shaft 205 and bend translation joint 300 can provide four types of movement, in other words, translation C and shaft twist D of the surgical device shaft 205 and bending E and translation F of the bend translation joint 300. Since the surgical device shaft 205 and the bend translation joint 300 can provide four types of movement C to F, the top end portion of the bend translation joint 300 has six degrees of freedom of a position and attitude. As a result, an arbitrary position and attitude is possible in a body cavity.

Figure 7:
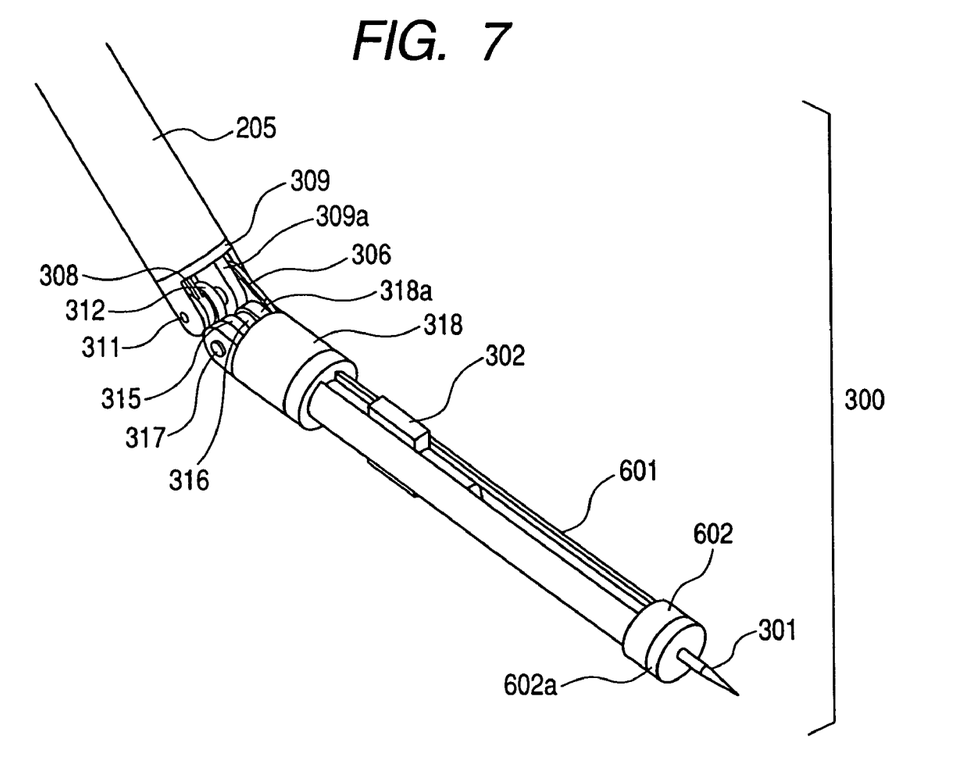
FIG. 7 shows a perspective view of the surgical device manipulator.

FIG. 7 is a detailed perspective view of the bend translation joint 300 forming a part of the manipulator 102. The cylindrical translation guide 318 is provided to a periphery of a joint positioned on an end portion of the surgical device shaft 205, the joint being a part of the bend translation joint 300. A puncture needle guide lid 602 whose center portion has a hole is placed distally of the translation guide 318. The translation guide 318 and the puncture needle guide lid 602 hold both ends of a puncture needle guide 601 having two plates each of which has a circular arc shaped section. The puncture needle guide 601 sandwiches projections formed on both sides of the shank 302. The puncture needle 301 moves through a hole formed in the puncture needle guide lid 602.

The puncture needle 301 shown in FIG. 3 in detail, the shank 302 connected to the puncture needle 301, and the rack 303 are integrated with each other to translate along the puncture needle guide 601 by using the projections of the shank 302 as guides. When a surgical device of, e.g., the puncture needle 301 is exchanged, a screw clamp between the puncture needle guide 601 and the puncture needle guide lid 602 is removed, and the puncture needle guide lid 602 is removed. After that, the small gear 316 is rotated to fully push out the rack 303 toward the puncture needle 301. Then, the puncture needle 301 and so on is removed from the puncture needle guide 601.

According to this embodiment, a different top end surgical device such as one having a different needle diameter can be exchanged. Since the puncture needle guide 601 and the puncture needle guide lid 602 are fastened by a screw, a surgical device is easily removed or exchanged. A ring-shaped marker 602a which can be recognized by a diagnosis apparatus such as an MRI apparatus is placed to the top end portion of the puncture needle guide lid 602. At this time, the ring-shaped marker 602a is placed so that the puncture needle 301 passes through a hole portion of the ring-shaped marker 602a. The ring-shaped marker 602a can be used for correcting a coordinate system of a surgical device manipulator and a coordinate system of a diagnosis apparatus, and for, e.g., marks on an MRI image.

In the correction of the two coordinate systems, by use of a difference between a position of the top end portion of the surgical device, the position being calculated on the coordinate system of the surgical device manipulator and displayed on an MRI diagnosis image, and a position of the actually placed marker 602a, an accuracy of each joint of the manipulator is corrected or evaluated. Even when the marker 602a having a short sensing life is used, the puncture needle 301 does not need to be dismantled when the marker 602a is exchanged. This is because the marker 602a is not attached to the puncture needle 301. Therefore, the marker 602a is easily exchanged.

Figure 8:
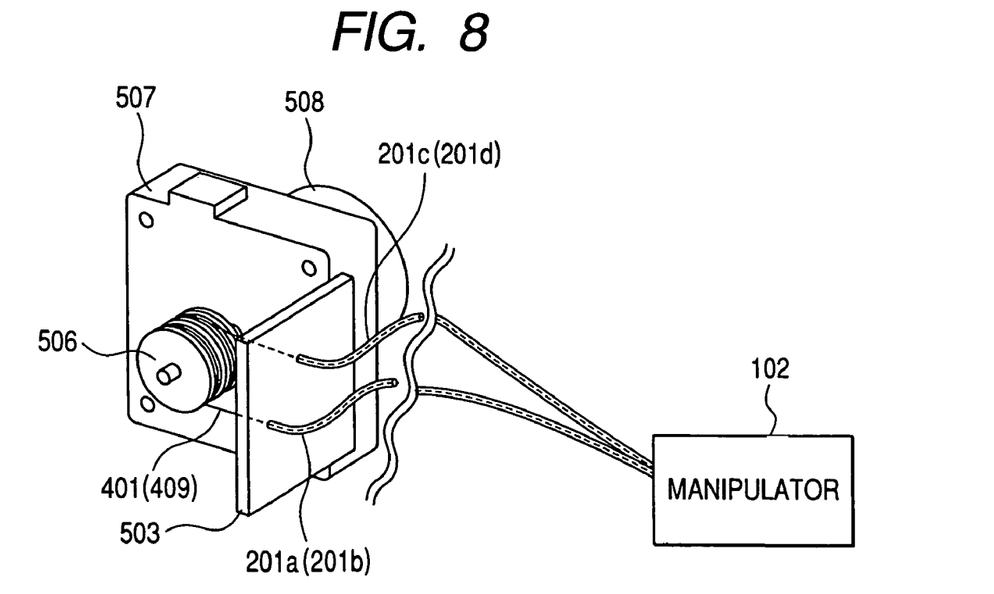
FIG. 8 is a perspective view of a driving portion for the surgical device.
Figure 9:
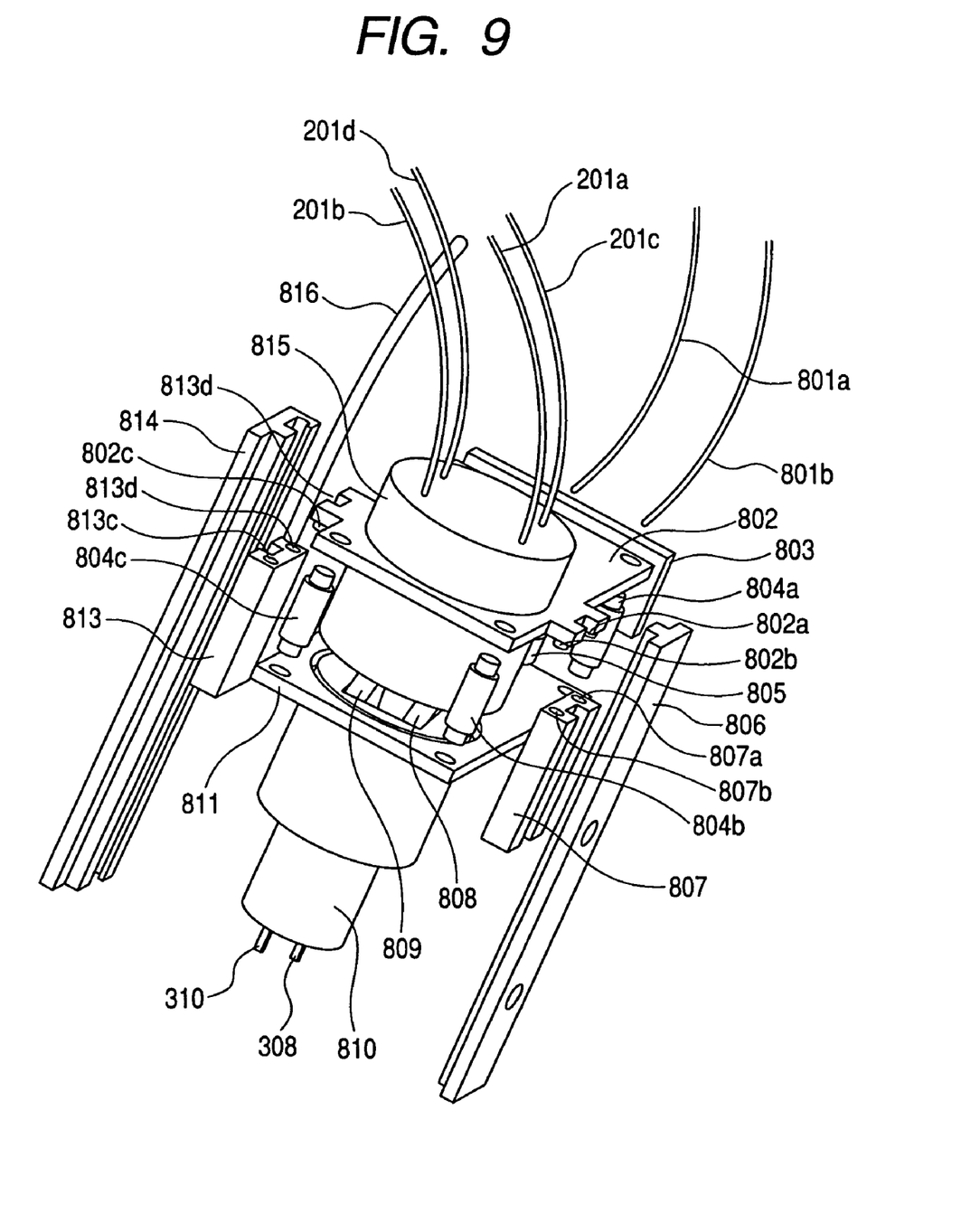
FIG. 9 is an exploded perspective view of the wire driving portion.
Figure 10:
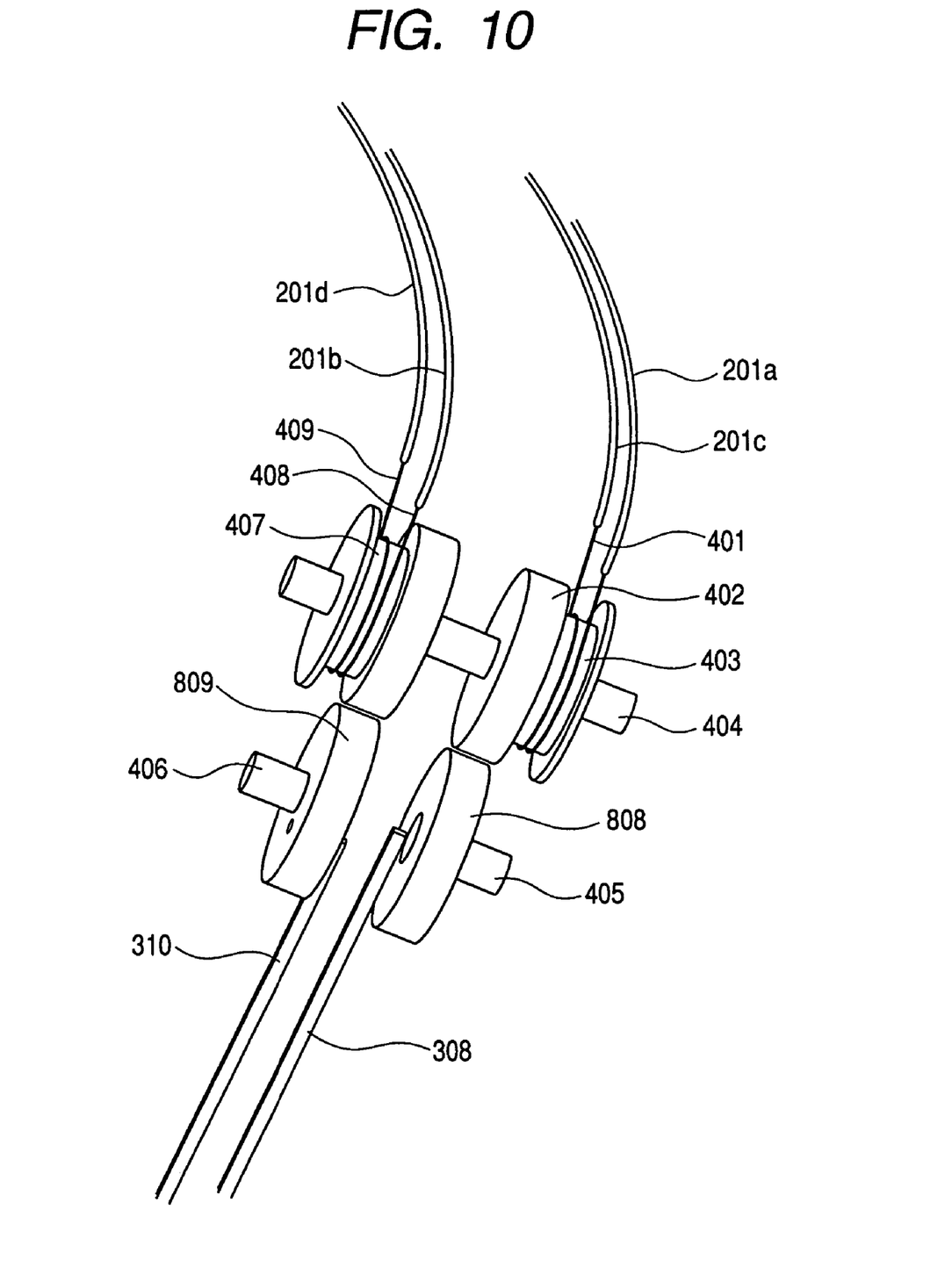
FIG. 10 is a perspective view of an inside of the wire driving portion for the surgical device.

FIGS. 7 to 10 shows the bend translation joint 300 in detail. FIG. 7 is a detail perspective view of the bend translation joint 300 forming a part of the manipulator 102. FIG. 8 is a perspective view of a driving source used for the bend translation joint 300. FIG. 9 is an exploded perspective view of the surgical device drive transmission portion 202. FIG. 10 is a perspective view of an inside of FIG. 9.

To achieve the translation C shown in FIG. 6, the manipulator 102 includes the following structure. Prismatic links 227 and 228 placed on a base side of the manipulator 102 have a pair of projecting portions 227a and 228a on their side end portions. Bearings for rotatably supporting pins 203 and 204 are held near projecting ends of the projecting portions 227a and 228a. By use of the pins 203 and 204, a planar translation guide 806 having a T-shaped section and a planar translation guide 814 having a F-shaped section, detailed shapes of the guides being shown in FIG. 9, are connected to the links 227 and 228, respectively. The links 227 and 228 rotates freely relative to the translation guides 814 and 806.

Linear projections of the translation guides 806, 814 are directed inside. Translation blocks 807 and 813 having grooves fitted to these projections are formed inside the translation guides 806, 814. A flexible rack 816 is connected to a side of the translation block 813, the side being opposed to a surgical device. The rack 816 passes through a guide tube (not shown), and is introduced to an ultrasonic motor (not shown) placed outside the MRI apparatus. The rack 816 engages a pinion attached to a shaft of the ultrasonic motor. When the ultrasonic motor moves the rack 816, the translation block 813 executes the translation C on the translation guide 814.

To achieve the shaft twist D shown in FIG. 6, the manipulator 102 has the following structure. As shown in FIG. 9, a surgical device adaptor 810 formed in a stepped cylindrical shape is placed to a side end portion of the surgical device shaft 205, the portion being opposed to the puncture needle. A flange 811 is provided on an upper surface of the surgical device adaptor 810. Stepped spacer shafts 804a to 804d are fitted to holes formed to four corners of the flange 811. Steps are formed also on upper ends of the spacer shafts 804a to 804d, and fitted to holes of a surgical device twist shaft guide 802, which is a flange member whose four corners have holes.

The surgical device twist shaft guide 802 is positioned on an axial middle portion of a cylindrical gear-wire conversion guide 815. Cylindrical projections 802a to 802d are formed on a lower surface of the surgical device twist shaft guide 802. The cylindrical projections 802a to 802d are fitted to holes 807a, 807b, 813c, and 813d formed on both ends of upper surfaces of the translation blocks 807, 813. Holes are formed on an upper surface of the gear-wire conversion guide 815. Resin flexible tubes 201a to 201d through which wires for driving a driving mechanism provided in the gear-wire conversion guide 815 are inserted, penetrate the holes.

The gear 805 integrated with a pulley (not shown) is placed to a space formed between the flange 811 and the surgical device twist shaft guide 802, the space being a back side of FIG. 9. The gear 805 engages a gear portion (not shown) formed to the gear-wire conversion guide 815. Resin wires (not shown) passing through the resin flexible tubes 801a and 801b are wound about the pulley integrated with the gear 805. When the resin wires are driven by means of a tendon-sheath transmission method, the pulley and the gear 805 rotate, and the gear-wire conversion guide 815 engaging the gear 805 rotates. As a result, the shaft twist D of the surgical device shaft 205 is generated.

The lower end portion of the cylindrical gear-wire conversion guide 815 is detachably fitted to a hole formed to the flange 811 of the surgical device adaptor 810. When the cylindrical gear-wire conversion guide 815 is fitted to the surgical device adaptor 810, gears 402, 408 engage gears 808, 809. By use of such a detachable structure, the surgical device 205 including the bend translation joint 300 is easily exchanged, improving the maintainability. Since only the surgical device shaft 205 is removed, any surgical device having gears which engage the gears 402, 408 can be used even if a top end of the device has a different shape. Accordingly, a shape of a surgical device is less limited, and thus many types of surgical device can be used. Since the surgical device can be removed, only the surgical device needs to be sterilized. The time for sterilization can be saved, and a sterilization apparatus can be made compact.

FIG. 10 shows an inner structure of the gear-wire conversion guide 815. Pulleys 403, 407 on which the resin wires 401, 409 in the flexible tubes 201a to 201d introduced through the holes formed to the gear-wire conversion guide 815 are mounted are formed to the pin 404. Gears 402, 408 having a diameter larger than that of the pulleys 403, 407 are formed axially inwardly of the pulleys 403, 407, and integrated with the pin 404 and the pulleys 403, 407.

A gear 808 engaging the gear 402 and a gear 809 engaging the gear 408 are placed adjacent the gears 402, 408, respectively. The gears 808, 809 are held in the surgical device adaptor 810 via the pins 405, 406. One end portion of each of the links 308 and 310 for driving the bend translation joint 300 is rotatably attached to each inner surface of the gears 808, 809 by use of pins (not shown).

The wires 401, 409 are introduced in the pulley 506 attached to the ultrasonic motor 508 shown in FIG. 8. A decelerator 507 is attached to the ultrasonic motor 508. A pulley 506 is attached to an output shaft of the decelerator 507. A bracket 503 to which the motor 508 is attached is attached to a side portion of the decelerator 507. The wires 401, 409 introduced to the pulley 506 are driven by means of a tendon-sheath transmission method. When the resin wires 401, 409 are driven, the pulleys 403, 407 and the gears 402, 408 integrated with the pulleys 403, 407 rotate about the pin 404.

Distances between shafts of pins (not shown) used for attaching the links 308, 310 which drive the bend translation joint 300 to the gears 808, 809 and shafts of the pins 405, 406 are the same as a distance between the end portion fixing pin 307 of the gear driving link 308 and the gear fixing pin 311. The distance is the same as a distance between the end portion fixing pin 307 of the gear driving link 308 and an end portion fixing pin (not shown) of the plate driving link 310. Accordingly, when the gears 808, 809 contained in the gear-wire conversion guide 805 rotate, the gear 312 and the plate 306 in the bend translation joint are driven.

Figure 11:
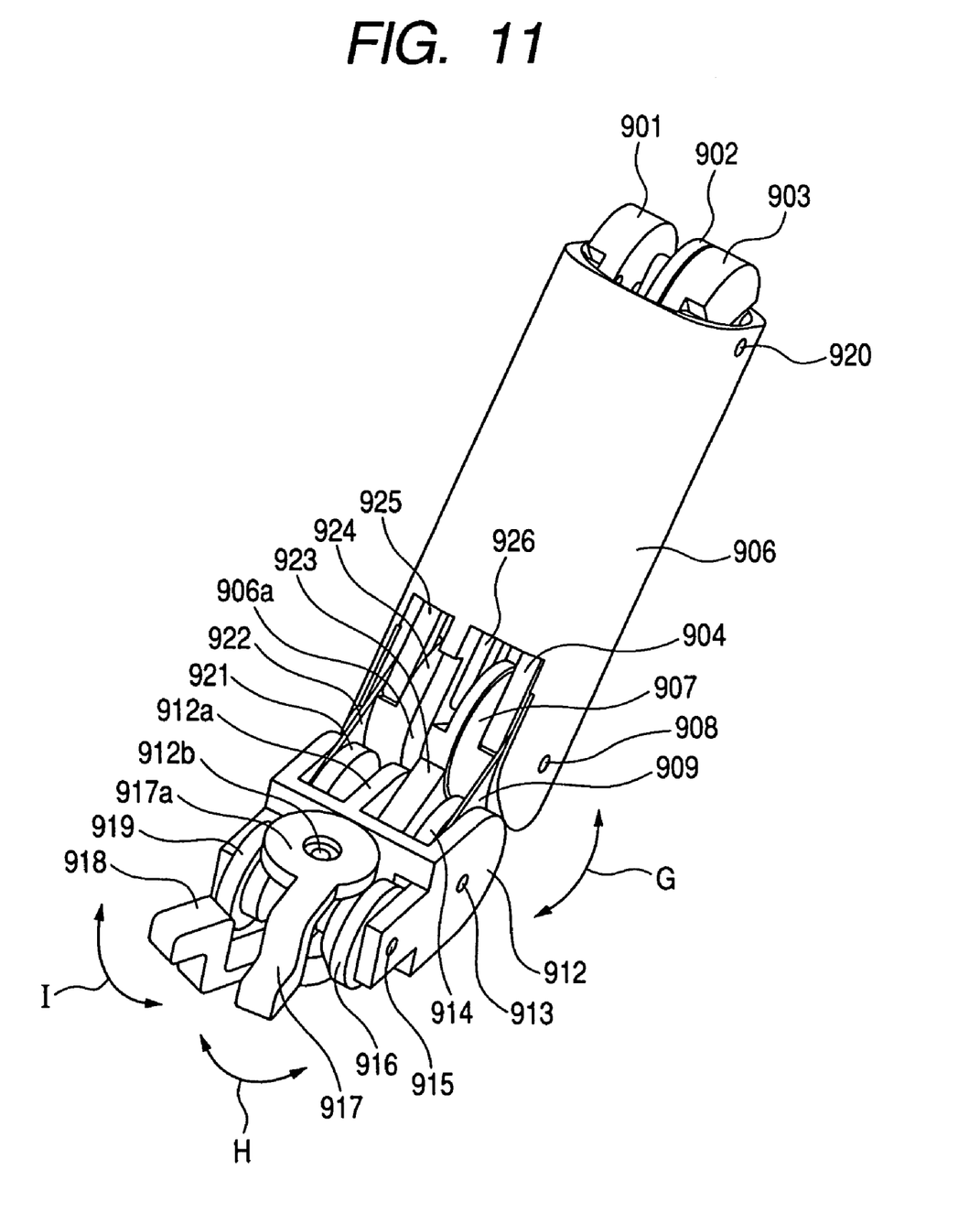
FIG. 11 is a perspective view of another embodiment of a surgical device used for the surgical device manipulator.
Figure 12:
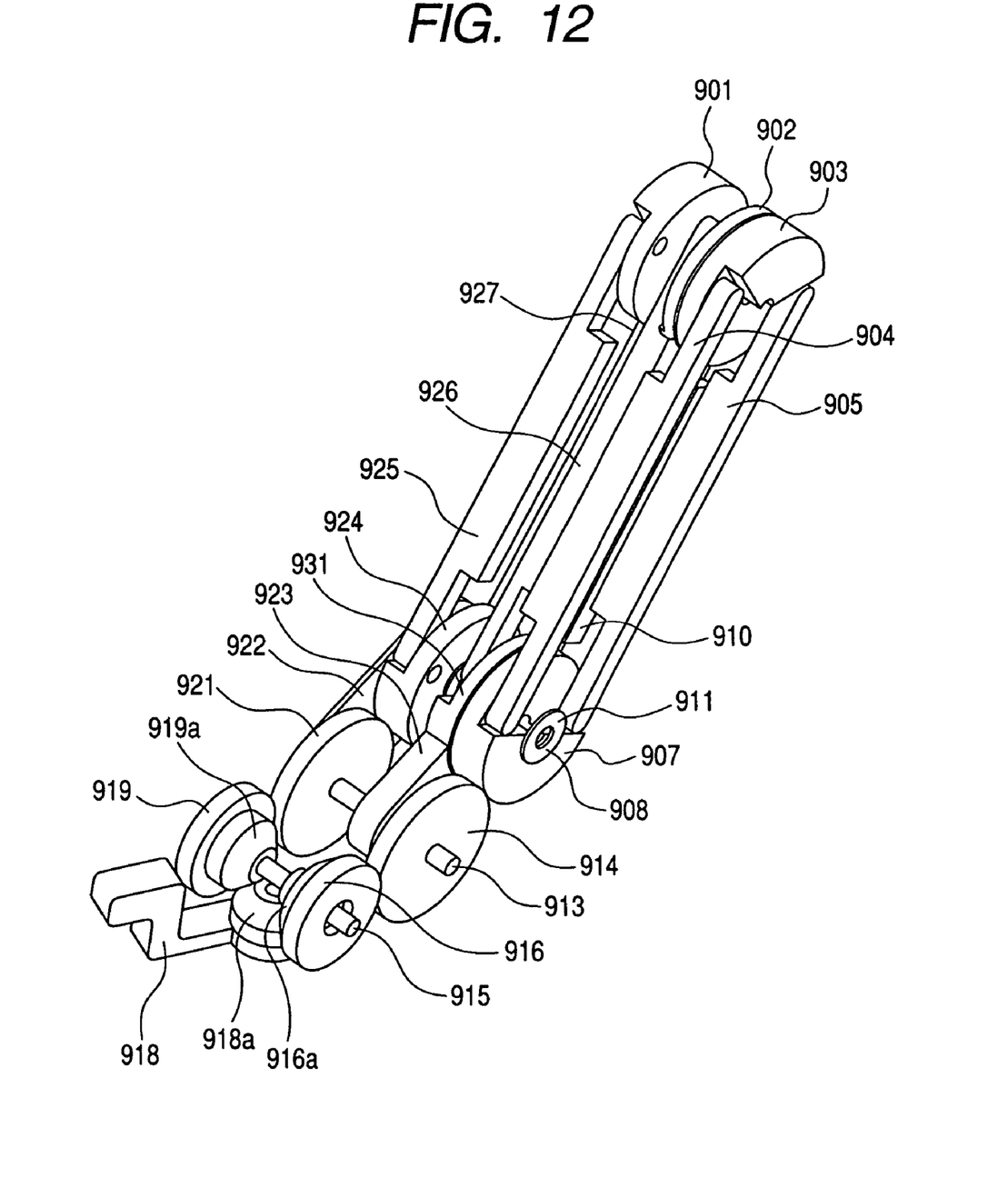
FIG. 12 is an inner perspective view of another embodiment of the surgical device used for the surgical device manipulator.

Another embodiment of the surgical operation apparatus of the present invention is explained in reference to FIGS. 11, 12. A difference between this embodiment and the above-described embodiment is that degrees of freedom of the top end portion of the surgical device increase by one. Accordingly, the surgical device has three degrees of distal freedom. FIG. 11 is a perspective view of a bend grip joint 900 used instead of the bend translation joint 300. FIG. 12 is a perspective view of a main portion of the bend grip joint 900 where a cover portion such as a surgical device cylinder 906 of the bend grip joint 900 is removed. Like the bend translation joint 300, the bend grip joint 900 can execute a bend movement G, and simultaneously execute grip movements H, I simulating scissors or tweezers without interfering the bend movement G. The bend grip joint 900 executes the grip movements H, I of two degrees of freedom cooperatively, so that gripping becomes possible.

An end portion of the bend grip joint 900, the end portion being on a side of a portion connected to the surgical device shaft 205, has three gears 901 to 903 engaging gears provided on a side of the surgical device shaft 205. The gears 901 to 903 are attached to a pin 920. Two links 925, 926 are placed in parallel on an outer side surface of the gear 901 positioned on the most left side. Two links 904, 905 are placed in parallel on an outer side surface of the gear 903 positioned on the most right side. Two links 926, 910 are placed in parallel on one side surface of the gear 902 positioned on the center. End portions of the links 925 to 927, 904, 905, and 910 are rotatably attached to the sides of the gears 901 to 903 by use of pins. Engagement portions of the gears 901 to 903 are made thick in the width direction, but their portions corresponding to movable ranges of the links 925 to 927, 904, and 905, are made thin in the width direction. The links 925 to 927, 904; and 905 are made thin on their portions opposing to the gears 901 to 903. Accordingly, the bend grip joint 900 is made compact. Peripheries of the links 925 to 927, 904, and 905, and 910 are covered with the surgical device cylinder 906.

Other end portions of the links 925 to 927, 904, and 905, and 910 are rotatably attached to sides of gears 924, 907, and roller 931 coaxially attached to a shaft 908. Therefore, the links 925 to 927, 904, and 905, 910, the gears 901 to 903, 924, 907, and roller 931 form three parallel link mechanisms. When a rotation angle of the gear 903 becomes larger, the links 904, 905 forming the parallel link interfere with each other to obstruct a rotation of the gear 903. Rotatable angles of the gears 901 to 903 depend on thicknesses of the links 904, 905, but are limited to about plus minus 60 degrees.

When the links 904, 905 are oppositely placed on both sides of the gear 903, the interference of the links 904, 905 can be prevented. When a rotation angle of the gear 903 becomes larger, the links 904, 905 interfere with the shaft 920. As a result, rotatable angles of the gears 901 to 903 are limited to about plus minus 60 degrees.

Lower end portions of the links 925 to 927, 904, and 905, and 910, as well as the upper end portions, are made thin on their portions opposing to opposing portions of the gears 907, 924 and the roller 931. Engagement portions of the gears 907, 924 and the roller 931 and their contact portions with the driving plate 923 are made thick in the axial direction, and the other portions are made thin. Both ends of the shaft 908 to which the gears 907, 924, and the roller 931 are supported by the surgical device cylinder 906 via the spacer 911 for reducing frictional resistance.

A gear 921 engaging the gear 924, a gear 914 engaging the gear 907, and a driving plate 922 which is in contact with the roller 931 and to which the same shape as that of the roller is formed, are attached to a shaft 913. The gear 921 engages the small gear 919 on the top end side. The gear 914 engages the small gear 916 on the top end side. The small gears 916, 919 are attached to the shaft 915, and spaced from each other. The small gears 916, 919 are rotatable relative to the shaft 915. Therefore, the small gears 916, 919 are separately rotatable without interfering with each other.

The both end portions of the shafts 913, 915 are supported by a top end bracket 912. Plates 922, 909 for connecting the surgical device cylinder 906 and the surgical device portion are placed inside a top end portion of the surgical device cylinder 906 and to an inside of the top end bracket 912, the inside being on a side of the surgical device cylinder 906. Shafts 908, 913 penetrates the plates 922, 909.

On the sides to which the surgical device cylinder 906 and the top end bracket 912 are opposed, and at a middle portion in the direction of the shafts 908, 913, rolling contact portions to which gears 906a and 912a engaging each other are partially formed are formed. The rolling contact portions enable the portion of the surgical device cylinder 906 and the portion of the surgical device to be in rolling contact with each other to rotate without sliding on each other. In this embodiment, the gears 906a, 912a are used for the rolling contact portions. Instead of the gears 906a, 912a, discs in rolling contact with each other without sliding on each other, and semicircular discs in rolling contact with each other without sliding on each other, rubber and so on being attached to surfaces of the semicircular discs, may be used. The rolling contact portions are formed in semicircular shapes about the pins 908, 913.

Axially inside the small gears 919, 916, small bevel gears 919a, 916a are attached to a shaft 915 and spaced from each other. A small bevel gear 918a engaging both of the two small bevel gears 919a, 916a is placed below the shaft 915. Another small bevel gear 917a (not shown in FIG. 12) engaging both of the two small bevel gears 919a, 916a is placed below the shaft 915. The small bevel gears 916a to 919a form a differential gear unit.

Grip portions 917, 918 are formed integrally with the small bevel gears 917a, 918a placed one above the other, and outwardly project from one circumferential portion of the small bevel gears 917a, 918a. The grip portions 917, 918 rotate about a pin 912b projecting upward and a pin projecting downward, the pins being provided to the top end bracket 912. A member such as a spacer 911 for reducing frictional resistance are always sandwiched between a gear and rotor arranged in the axial direction, such as between the gear 924 and the rotor 931 and between the rotor 931 and the gear 907.

In the surgical device cylinder portion and surgical device portion structured as described above, when the gear 902 is rotated, the driving plate 923 tries to rotate about the shaft 908 by means of the parallel link mechanism. At this time, the shaft 913 connected to the driving plate 923 revolves about the shaft 908 while maintaining a distance between the shafts 908 and 913. In this case, the top end bracket 912 connected to the shaft 913 tries to rotate. However, since the gears 906a and 912a engage each other, the top end bracket 912 rotates about the shaft 913 while revolving about the shaft 908. The gear 906a of the surgical device cylinder 906 and the gear 912a of the top end bracket 912 are in rolling contact with each other to rotate.

Since the positions of the gears 901, 903 are fixed, the gears 924, 921 rotate in rolling contact with each other, and the gears 907, 914 rotate in rolling contact with each other. These movements are the same as the bending movement shown in FIGS. 3, 4. Since positions of the gears 921, 914 do not change relative to the top end bracket 912, the gears 921, 914 and the grip portions 918, 917 bend with maintaining their predetermined positions.

To execute the grip movements H, I, the gears 901, 903 on the both ends are driven. For example, when the gear 901 on the left side is moved, the gear 924 is driven. With this drive, the gears 921, 919, the bevel gears 919a, 918a, and the grip portion 918 are driven to execute the grip movement I independently of the bending movement G. When the gear 903 on the right side is moved, the gear 907 is driven. The gears 914, 916, the bevel gears 916a, 917a, and the grip portion 917 are driven to execute the grip movement H independently of the bending movement G.

Diameters of the bevel gears 916a, 919a integrated with the gears 916, 919 are changed to prevent interference of the bevel gears 917a, 918a integrated with the grip portions 917, 918. The joints H, I can be driven separately. When a deceleration ratio of the gears 914, 916 is set to 1.5, the grip portion 917 can move by plus minus 90 degrees even if a movable range of the gears 903, 907, and 914 is plus minus 60 degrees. The grip portion 918 can move like the grip portion 917.

According to this embodiment, since movements of the top end of the surgical device are achieved by use of the links and the rolling contact mechanisms, three degrees of freedom of the top end of the surgical device can be driven separately without wires. Since no wire is used for the surgical device portion, no breakage and so on occurs due to slack and fatigue of the wires. The controllability and maintainability of the medical manipulator are improved. Since the joints can be driven separately, the controllability and stability of the manipulator can be improved.

Figure 13:
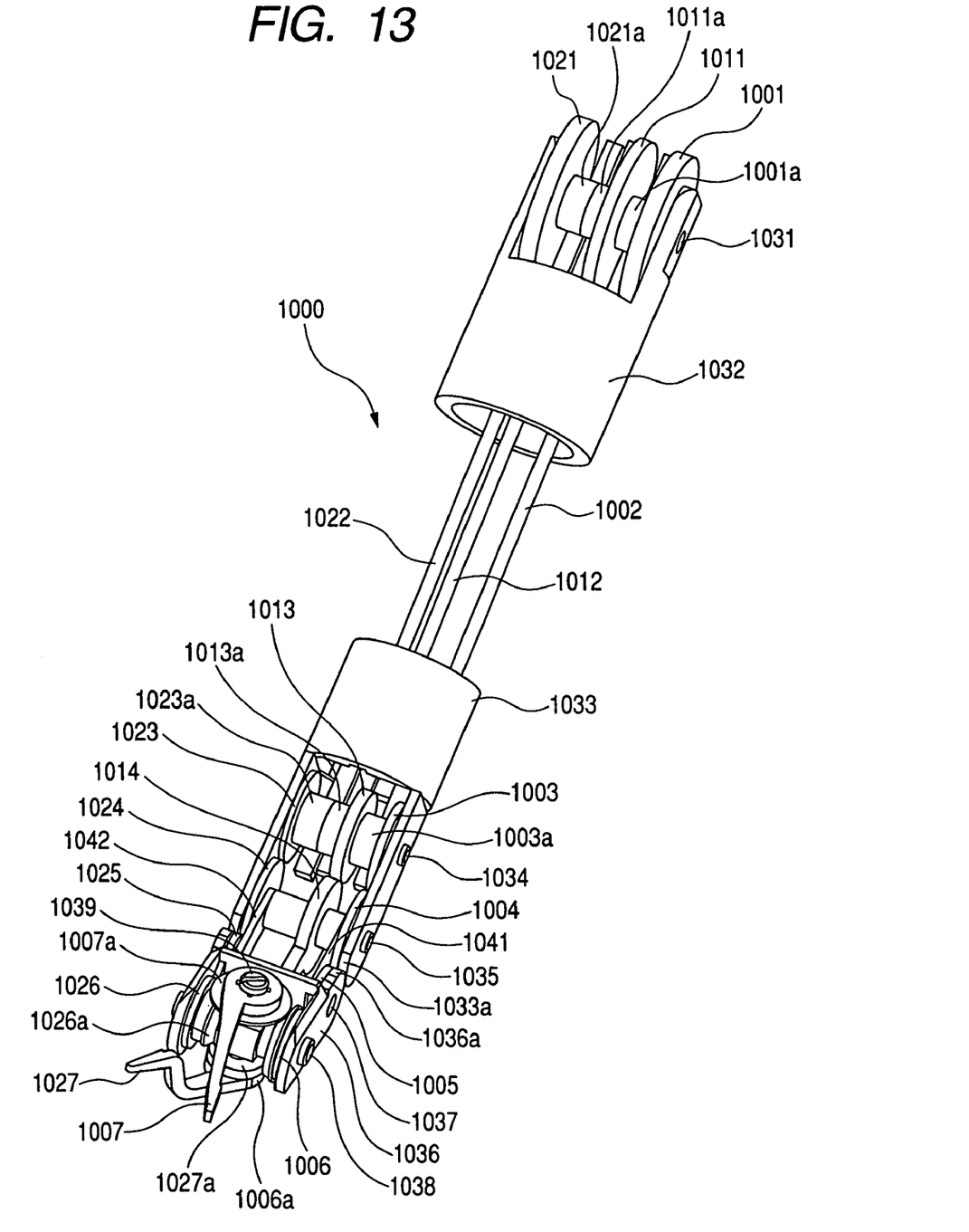
FIG. 13 is a perspective view of another embodiment of the surgical device manipulator of the present invention.

FIG. 13 is a perspective view of another embodiment of a bend translation joint 1000 of the present invention. In the above embodiment, the bend translation joint is driven by use of the parallel link mechanism. In this embodiment, the manipulator is driven by use of a rack-and-pinion mechanism. A root portion of the bend translation joint 1000, the root portion being an attachment end for the surgical device shaft 205, is covered with a bracket 1032. A middle portion covered with a cylindrical bracket 1033 and a cylindrical bracket (not shown) connects between the root portion and the surgical device portion, which is the top end portion. The cylindrical bracket (not shown) maintains a distance between the bracket 1032 of the root portion and the bracket 1033 of the middle portion constant.

A plurality of gears 1001 to 1021 are coaxially attached to a shaft 1031 on the end portion on the root portion of the bend translation joint 1000 to transmit a driving power from the surgical device shaft to the surgical device portion. A pinion 1001a is placed between the gears 1001 and 1011. Pinions 1011a, 1021a are placed between the gears 1011 and 1021. The gear 1001 is integrated with the pinion 1001a. The gear 1011 is integrated with the pinion 1011a. The gear 1021 is integrated with the pinion 1021a.

One end side of each of racks 1002 to 1022 extending to the side of the surgical device engages each pinion 1001a to 1021a. The other end side of each of the racks 1002 to 1022 engages each of the pinion 1003a to 1023a placed on a middle portion of the bend-translation joint 1000. The pinion 1003a is integrated with the gear 1003. The pinion 1013a is integrated with the gear 1013. The pinion 1023a is integrated with the gear 1023. The pinions 1003a to 1023a and the gears 1003 to 1023 are attached to a first shaft 1034 on the middle portion.

Gears 1004, 1024 engaging gears 1003, 1023 placed on both end portions of the first shaft 1034 on the middle portion are attached to a second shaft 1035 in parallel with the first shaft 1034 and placed closer to the surgical device side than the first shaft 1034. The gear 1013 placed on the middle of the first shaft 1034 engages a gear portion formed to a part of a driving plate 1014. The driving plate 1014 is attached to the second shaft 1035. Elliptical plates 1041, 1042 are attached to both end portions and axially inside the gears 1004, 1024. A gear 1033a concentric with the second shaft 1035 is partially formed to two circumferential portions of the end portion of the bracket 1033 on the middle portion, the two portions being on the side of the surgical device.

The end portions on the middle portion and on the surgical device side engage gears attached on the surgical device side. In other words, elliptical top end brackets 1036 are placed on both outer surfaces of the surgical device side. A gear 1036a is partially formed to an end portion of the middle portion of the top end bracket 1036, the end portion being on the surgical device side. A first shaft 1037 of the surgical device portion and a second shaft 1038 on the surgical device side are attached to the top end bracket 1036. Pinions 1005, 1025 engaging the gears 1004, 1024 attached to the second shaft 1035 on the middle portion, and elliptical plates 1041, 1042, are attached to the first shaft 1037 on the surgical side.

The surgical device and a portion to which the surgical device is attached have the same structure as those shown in FIGS. 11, 12. The gears 1006, 1026 and the bevel gears 1006a, 1026a are attached to the second shaft on the surgical device side sequentially inwardly from the side of the top end bracket 1036. The gear 1006 is integrated with the bevel gear 1006a. The gear 1026 is integrated with the bevel gear 1026a. The gear 1006 engages the gear 1005 attached to the first shaft 1036 on the surgical device. The gear 1026 engages the gear 1025.

Bevel gears 1007a, 1027a respectively integrated with plates 1007, 1027 are attached to a shaft 1039 extending in a direction orthogonal to a second shaft 1038 to which the bevel gears 1006a, 1026a are attached. The bevel gears 1007a, 1027a are opposed to each other. The shaft 1039 to which the bevel gears 1007a, 1027a in the orthogonal direction are attached is attached to a second shaft 1038 on the surgical device side.

In the bracket 1033 placed on the middle portion and the top end bracket 1036 placed on the surgical device side, a distance between the second shaft 1035 on the middle portion and the first shaft 1037 on the surgical device side is maintained constant by use of the elliptical plates 1041, 1042 and the driving plate 1014. The bracket 1033 placed on the middle portion and the top end bracket 1036 do not slide on each other, but are in rolling contact with each other, because the gears 1033*a*, 1036*a* respectively formed to the bracket 1033 and the top end bracket 1036 engages each other.

Movements of the bend translation joint 1000 structured as described above are explained below. When the gear 1001 attached to the shaft 1031 on the root side is driven to rotate, the pinion 1001*a* pivots to move the rack 1002 in the axial direction of the bend-translation joint 1000. Then, the pinion 1003*a* attached to the first shaft 1034 on the middle portion pivots, and the gear 1003 integrated with the pinion 1003*a* also pivots.

Since the gears 1003 to 1006 form a gear train, the bevel gear 1006*a* integrated with gear 1006 also pivots. Since the bevel gear 1006*a* engages the gear 1027*a* on the upper side, a blade 1007 on the upper side, the blade 1007 being integrated with the bevel gear 1007*a*, oscillates. In the same way, the gear 1021 is driven to rotate, the blade 1027 on the lower side oscillates.

When the gear 1011 placed on the middle portion of the shaft 1031 on the root side is driven to rotate, the gear 1013 attached to the first shaft 1034 on the middle portion pivots, as well as the gears 1001, 1021. Since the gear partially formed to the driving plate 1014 engages the gear 1013, the driving plate 1014 pivots. Since the driving plate 1014 is attached to the first shaft 1037 on the surgical device side, the first shaft 1037 on the surgical device side pivots about the second shaft 1035 on the middle portion. At this time, a distance between the second shaft 1035 on the middle portion and the first shaft 1037 on the surgical device side is maintained constant by use of the driving plate 1014.

Since the gear 1036*a* formed to the top end bracket 1036 engages the gear 1033*a* formed to the bracket 1033 on the middle portion, the brackets 1036, 1033 do not slide on each other, but are in rolling contact with each other. Therefore, the top end bracket 1036 revolves about the second shaft 1035 on the middle portion while rotating about the second shaft 1036 on the surgical device side.

The gears 1005, 1025 attached to the first shaft 1037 on the surgical device side, the gears 1005, 1025 forming the gear train, revolve about the gears 1004, 1024 while not sliding on the gears 1004, 1024, but being in rolling contact with the gears 1004, 1024. Therefore, the movement of the driving plate 1014 receives no influence. As a result, the blades 1007, 1027 forming the surgical device can pivot independently of the bending movement of the surgical device portion.

According to this embodiment, after a joint is bent, a surgical device provided to an oscillating shaft which is placed orthogonal to the bent joint can oscillate. Therefore, the movements does not interfere with each other. Since no wire is used for the driving power, slack, wear, and breakage of wires do not occur, and the maintainability is improved.

What is claimed is:

1. A surgical operation apparatus including a manipulator having three degrees of distal freedom,
wherein the manipulator includes a joint portion having a plurality of degrees of freedom which can bend and translate in a body cavity of a patient while the bend and translation do not interfere with each other, and a driving power is transmitted from an outside of the joint portion to the joint portion by a link mechanism, and wherein the joint portion has a pair of gears engaged with each other, a plate member to which the pair of the gears are attached, a small gear integrally formed to one of the pair of the gears, a flexible rack engaged with the small gear, a first link whose one end portion is attached to the other of the pair of the gears, and a second link whose one end portion is attached to the plate member, and wherein a bending movement is made by driving the second link, and a translating movement is made by driving the first link.

2. The surgical operation apparatus according to claim 1, further comprising a driven gear attached to the other end portions of the first and second links, a driving gear in rolling contact with the driven gear, a pulley for driving the driving gear and a flexible wire mounted to the pulley.

3. A surgical operation apparatus comprising:
a diagnostic imaging apparatus for detecting a condition of a patient and visualizing the condition, wherein the diagnostic imaging apparatus is an MRI apparatus;
a surgical device accessible to a diseased area of a patient;
a manipulator having three degrees of distal freedom whose top end portion has the surgical device; and
a control portion for driving and controlling the manipulator,
wherein the manipulator includes a joint portion having a plurality of degrees of freedom which can bend and translate in a body cavity of a patient, and wherein a driving power is transmitted from outside of the joint portion to the joint portion by a link mechanism.

4. The surgical operation apparatus according to claim 3, wherein markers which can be recognized by the MRI apparatus are placed on a guide member for guiding a translation surgical device which is near the surgical device and exchangeable.

* * * * *